(12) United States Patent
Cravo et al.

(10) Patent No.: US 8,742,103 B2
(45) Date of Patent: Jun. 3, 2014

(54) SEPARATION OF TRIAZINE DERIVATIVES ENANTIOMERS USING TARTARIC ACID

(75) Inventors: Daniel Cravo, Montesson (FR); Matthias Helmreich, Heidelberg (DE)

(73) Assignee: Poxel, Lyons (FR)

( * ) Notice: Subject to any disclaimer, the term of this patent is extended or adjusted under 35 U.S.C. 154(b) by 0 days.

(21) Appl. No.: 13/990,924

(22) PCT Filed: Nov. 30, 2011

(86) PCT No.: PCT/EP2011/071347
§ 371 (c)(1),
(2), (4) Date: May 31, 2013

(87) PCT Pub. No.: WO2012/072663
PCT Pub. Date: Jun. 7, 2012

(65) Prior Publication Data
US 2013/0261300 A1     Oct. 3, 2013

(30) Foreign Application Priority Data
Dec. 1, 2010  (EP) .................................... 10306327

(51) Int. Cl.
*C07D 251/24* (2006.01)
*A61K 31/53* (2006.01)
*A61P 3/04* (2006.01)

(52) U.S. Cl.
USPC ............ 544/204; 544/206; 544/208; 544/209

(58) Field of Classification Search
USPC .................................. 544/204, 206, 208, 209
See application file for complete search history.

(56) References Cited

U.S. PATENT DOCUMENTS 7,501,511 B2 *   3/2009   Moinet et al. ................. 544/206

FOREIGN PATENT DOCUMENTS

WO      WO 2007/089917        10/2004

OTHER PUBLICATIONS

International Search Report for PCT/EP2011/071347 mailed Feb. 10, 2012.
Written Opinion of the International Searching Authority mailed Feb. 10, 2012.
J. Jacques et al., "Enantiomers, Racemates, and Resolutions, Passage", Jan. 1, 1981, pp. 256, 259/260.
S. Wacharine-Anter et al., "Resolution of ( )- Imeglimin-2, 4 Dichlorophenylacetate Menthanol Solvate by Preferential Crystallization", Organic Process Research & Development, vol. 14, No. 6, Nov. 19, 2010, pp. 1358-1363.

* cited by examiner

*Primary Examiner* — Venkataraman Balasubramanian
(74) *Attorney, Agent, or Firm* — Nixon & Vanderhye P.C.

(57) ABSTRACT

The present invention relates to a new process of separation of triazine derivatives enantiomers involving tartaric acid.

19 Claims, 1 Drawing Sheet

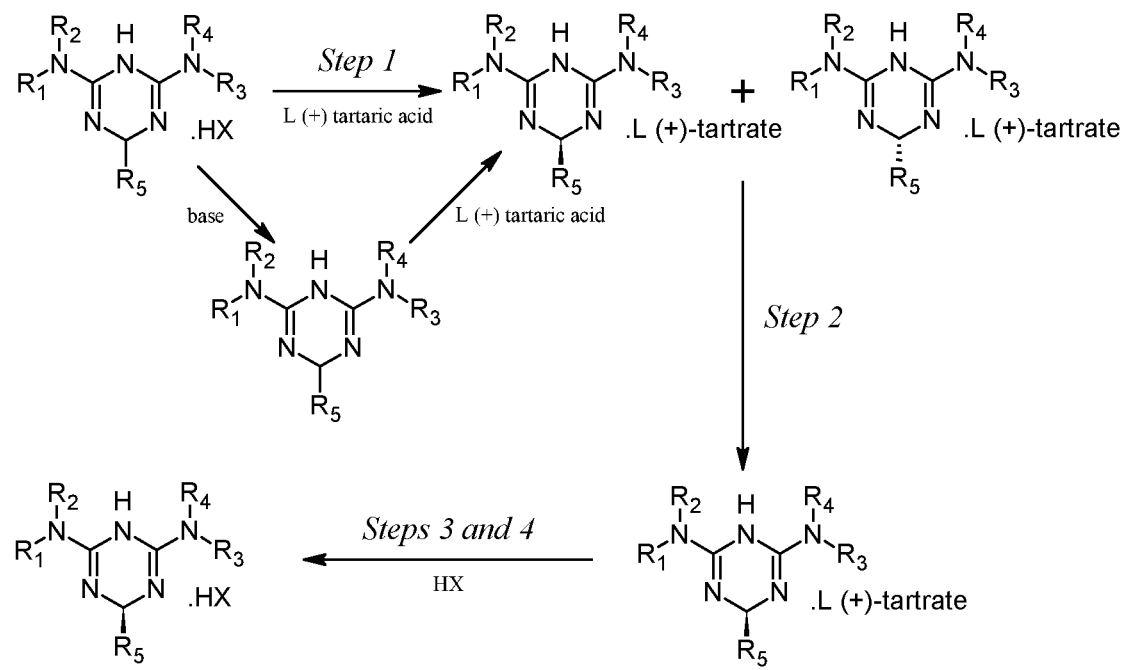

SEPARATION OF TRIAZINE DERIVATIVES ENANTIOMERS USING TARTARIC ACID

This application is the U.S. national phase of International Application No. PCT/EP2011/071347 filed 30 Nov. 2011 which designated the U.S. and claims priority to EP 10306327.7 filed 1 Dec. 2010, the entire contents of each of which are hereby incorporated by reference.

The present invention relates to a new process of separation of triazine derivatives enantiomers involving tartaric acid.

BACKGROUND OF THE INVENTION

Dihydro-1,3,5-triazines have been shown to be useful in the treatment of pathologies associated with insulin resistance, in particular type II diabetes (see WO2001/055122).

It is known that the biological activity of enantiomers of racemic compounds can differ considerably depending on the two enantiomers. Consequently, there is often one enantiomer that has more pronounced activity, making it more advantageous as an active principle in a medicament.

The use of this enantiomer instead of the racemate is advantageous. Specifically, the higher activity of the identified enantiomer makes it possible to reduce the dosage of active principle in the medicament. The lower dosage then allows a reduction of the adverse side effects. It is thus desirable for an active principle to be composed of only the pure enantiomer that has the largest desired biological effects.

Numerous methods exist for separating a racemic mixture into its two pure enantiomers. For further information in this respect, reference is made especially to the book "Chirotechnology" by R. A. Sheldon (1993) published by Dekker.

Examples of such processes that may be mentioned include:
- separation based on a physical property difference
- separation based on the use of biotechnological methods (whole cells, enzymes, etc.)
- separation based on the use of chromatographic methods
- separation based on the formation of diastereoisomers (salts, addition of a chiral centre).

Several processes have been described to date allowing separation of both enantiomers of dihydro-1,3,5-triazines. These enantiomers have been for instance separated by formation of diastereoisomeric salts (WO2004/089917), by particle size-controlled crystallization (PCT/EP2009/059769), and by preferential crystallization (PCT/EP2010/054037).

The previously described process involving formation of diastereoisomeric salts is specific of certain chiral reagents. In particular, the process requires the desired diastereoisomeric salt to selectively crystallize to be recovered from the medium, and that is not the case with all chiral reagents. The most efficient chiral reagents to be used in this process, such as di-O,O'-p-toluoyl-L-tartaric acid, are quite expensive and not as easily available as tartaric acid. Further, the starting material for this process is the triazine derivative under its free base form, and as usual preparation routes lead to the hydrochloride salt of the triazine derivatives, this process necessarily implies a step of re-formation of the free triazine derivative from the corresponding hydrochloride salt.

In this context, the Applicant surprisingly discovered a new process for separating enantiomers of the triazine derivatives by formation of diastereoisomeric salts, involving tartaric acid as chiral reagent. This process affords the separation of enantiomers in higher yield, with lower impurities and with lower expenses than the previously described process. The main drawbacks of the prior art process are actually overcome by the possibility to proceed directly from a salt of the triazine and by the unexpected crystallization of the desired dihydro-1,3,5-triazine salt.

DESCRIPTION OF THE INVENTION

The process of the invention involves a step of separation of enantiomers of triazine derivatives of formula (I) below:

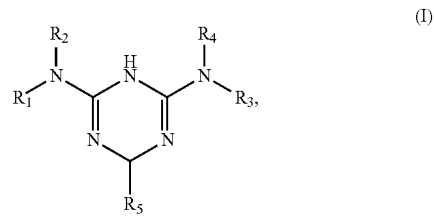

wherein:
$R_1$, $R_2$, $R_3$ and $R_4$ are chosen independently from the following groups:
H;
(C1-C20) alkyl optionally substituted by halogen, (C1-C5) alkyl, (C1-C5) alkoxy or (C3-C8) cycloalkyl;
(C2-C20) alkylene optionally substituted by halogen, (C1-C5) alkyl or (C1-C5) alkoxy;
(C2-C20) alkyne optionally substituted by halogen, (C1-C5) alkyl or (C1-C5) alkoxy;
(C3-C8) cycloalkyl optionally substituted by (C1-C5) alkyl or (C1-C5) alkoxy;
(C3-C8) heterocycloalkyl bearing one or more hetero atoms chosen from N, O and S and optionally substituted by (C1-C5) alkyl or (C1-C5) alkoxy;
(C6-C14) arylalkyl (C1-C20) optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
(C6-C14) aryl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl; or
(C5-C13) heteroaryl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl; $R_1$ and $R_2$, on the one hand, and $R_3$ and $R_4$, on the other hand, possibly forming with the nitrogen atom to which they are linked an n-membered ring (n between 3 and 8) optionally comprising one or more hetero atoms chosen from N, O and S and possibly being substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
$R_5$ is chosen from the following groups:
(C1-C20) alkyl optionally substituted by amino, hydroxyl, thio, halogen, (C1-C5) alkyl, (C1-C5) alkoxy, (C1-C5) alkylthio, (C1-C5) alkylamino, (C6-

C14) aryloxy, (C6-C14) arylalkoxy (C1-C5), cyano, trifluoromethyl, carboxyl, carboxymethyl or carboxyethyl;

(C2-C20) alkylene optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) aryl alkoxy (C1-C5), cyano, trifluoromethyl, carboxyl, carboxymethyl or carboxyethyl;

(C2-C20) alkyne optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;

(C3-C8) cycloalkyl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) aryl alkoxy (C1-C5), cyano, trifluoromethyl, carboxyl, carboxymethyl or carboxyethyl;

(C3-C8) heterocycloalkyl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;

(C6-C14) aryl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;

(C5-C13) heteroaryl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;

(C6-C14) arylalkyl(C1-C5) optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl, or a salt thereof.

Triazine derivatives of formula (I) wherein at least one of $R_1$, $R_2$, $R_3$ and $R_4$ is a hydrogen atom may be represented by their tautomer form. An example of tautomeric equilibrium is represented below in the case where $R_4$=H.

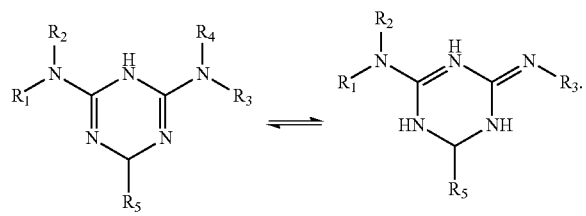

For one preferred subgroup of compounds of the formula (I), at least one of $R_3$ and $R_4$ is a hydrogen atom, the other of $R_3$ and $R_4$ being such as described above, in particular $R_3$ and $R_4$ are both hydrogen atoms.

For another preferred subgroup of compounds of the formula (I), $R_1$ and $R_2$ both independently represent a C1 to C3 alkyl group, advantageously methyl.

For one preferred subgroup of compounds of the formula (I), the triazine compound is in the form of a salt, in particular a hydrochloride salt.

In the present invention, the term "salt" of a triazine derivative refers to an acid addition salt formed by the reaction of the triazine derivative (as free base) with an acid. Among acid addition salts that may be considered can be cited bromhydrate, chlorhydrate, sulphate, bisulphate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamate, malonate, salicylate, propionate, methylenebis-b-hydroxynaphthoate, gentisic acid salt, isethionate, di-p-toluoyltartrate, methanesulfonate, ethanesulfonate, benzenesulfonate, p-toluenesulfonate, cyclohexyl sulfamate, quinateslaurylsulfonate, and the like (see for instance S. M. Berge et al. <<Pharmaceutical Salts>> J. Pharm. Sci, 66: p. 1-19 (1977)). In particular, the salt is hydrochloride salt. For the sake of clarity, the acid that can be used to form the salt may be generally written in the present description as HX. The corresponding amine salt will then be —NHR$_i$R$_j$$^+$X$^-$.

The compounds of formula (I) that are particularly preferred are: 2-amino-3,6-dihydro-4-dimethylamino-6-methyl-1,3,5-triazine and 2-amino-6-cyclohexyl-3,6-dihydro-4-dimethylamino-1,3,5-triazine, or one of their salts.

The compound of formula (I) that is highly preferred is 2-amino-3,6-dihydro-4-dimethylamino-6-methyl-1,3,5-triazine, in particular 2-amino-3,6-dihydro-4-dimethylamino-6-methyl-1,3,5-triazine hydrochloride.

The aim of the process according to the invention is to start with a mixture of both enantiomers of a triazine derivative of formula (I), or a salt thereof, and to separate both enantiomers in order to isolate a single enantiomer of a triazine derivative of formula (I), or a salt thereof.

The starting material of the process of the invention is a mixture of both enantiomers of a compound of formula (I), or a salt thereof. Preferably, the starting material is a racemic mixture of both enantiomers of a compound of formula (I), or a salt thereof. The racemic dihydro-1,3,5-triazine or the salt thereof may be synthesised according to already described processes, starting for instance from metformin. The international patent applications WO 2001/055122, WO 2009/095159 and WO 2009/141040 disclose methods for preparing the racemic dihydro-1,3,5-triazine. Preferably, the compound of formula (I) is in the form of a salt, in particular a hydrochloride salt.

The process according to the invention may comprise a preliminary step consisting of preparing the racemic dihydro-1,3,5-triazine salt, in particular hydrochloride salt, for instance according to one of the procedures described in one of the three above cited applications.

The process according to the invention comprises the following steps:

step 1: formation of a diastereoisomeric tartrate salt of the triazine derivative with a single enantiomer of tartaric acid, step 2: separation of both diastereoisomers of the tartrate salt, step 3: transformation of at least one isolated diastereoisomer of the tartrate salt into another salt, and step 4: recovery of the triazine salt obtained in step 3.

Step 1

Step 1 is the formation of a diastereosimeric tartrate salt of the triazine derivative with a single enantiomer of tartaric acid.

Formation of the tartrate salt of the triazine derivative is performed by reaction of the triazine derivative or its salt, preferably its hydrochloride salt, with a single enantiomer of tartaric acid (2,3-dihydroxybutanedioic acid). The single enantiomer of tartaric acid may be chosen among L-(+)-tartaric acid and D-(−)-tartaric acid, preferably L-(+)-tartaric acid. The naturally occurring form of the acid is L-(+)-tartaric acid. The mirror-image (enantiomeric) form, D-(−)-tartaric acid, can be made artificially.

When the process is performed with the triazine derivative (free base) as starting material, no base is necessary in the reaction medium.

When the process is performed with a salt of the triazine derivative as starting material, a base is preferably present in the reaction medium. Two different embodiments to perform the reaction may be used.

In a first embodiment, the salt of the triazine derivative, for instance the hydrochloride salt, is reacted with the enantiomer of tartaric acid and a base is present in the medium to trap formed acid (HX), for instance HCl, released by the reaction. Among the bases that may be used to trap the released acid may be cited alkylamines such as triethylamine and diethylamine, and alcoholamines such as ethanolamine, diethanolamine and triethanolamine. In a preferred embodiment, the base is triethylamine. In a highly preferred embodiment, the base is triethylamine and the triazine derivative salt is hydrochloride; under these conditions, the reaction is favoured by the solubility of triethylamine hydrochloride in the reaction medium.

In a second embodiment, the salt of the triazine derivative, for instance the hydrochloride salt, is first reacted with a base in order to release the corresponding triazine derivative as a free base, and then reacted with the enantiomer of tartaric acid. According to this embodiment, the formed salt, for instance NaCl, must be removed from the reaction medium, for example by filtration, preferably before the reaction with tartaric acid. Among the bases that may be used to release the free triazine derivative base may be cited sodium hydroxide and sodium methoxide.

Step 1 can be performed neat or in a solvent, it is preferably performed in a solvent.

The solvent of step 1 may be chosen among C1-C4 alcohols, water and mixtures thereof. Preferably, the solvent is chosen among methanol, ethanol, isopropanol and mixtures thereof. In particular, the solvent is methanol.

Step 1 is preferably performed at atmospheric pressure and at a temperature comprised between 20° C. and reflux temperature of the solvent or solvent mixture, for instance 80° C. In a specific embodiment, the temperature of the medium is kept under 30° C. when adding the base, the reaction mixture is then heated to reflux, and crystallization happens during a progressive decrease of the temperature, typically involving at least two plateau phases, for instance at 50-60° C. and 5-10° C.

Step 1 preferably leads to the crystallization of the desired diastereoisomer of the tartrate salt of the triazine derivative. The experimental conditions of step 1 can be adjusted to monitor the crystallization. In particular, the experimental conditions can be adjusted to favour the crystallization of one diastereoisomer of the tartrate salt. The other diastereoisomer remains for instance solubilised in the reaction medium.

It might be necessary to seed the reaction medium with crystals of the desired product, as classically performed in the art when a crystallization process does not spontaneously occur.

Step 2

Step 2 is the separation of both diastereoisomers of the tartrate salt. Step 2 corresponds more particularly to isolation of the desired diastereoisomer of the tartrate salt of the triazine derivative.

Step 2 corresponds in particular to recovering the crystals formed in step 1. Isolated crystals may be recovered more specifically by filtration, for instance using a dynamic filter dryer, or by centrifugation.

Typical molar yields for the sequence including steps 1 and 2 are in the range of 40 to 45%.

After recovery of one diastereoisomer, it is possible to re-process the remaining mixture in presence of the other enantiomer of tartaric acid. This embodiment may allow the second enantiomer of the triazine derivative to be isolated.

In an embodiment, the sequence comprising steps 1 and 2 is performed n consecutive times, in order to increase the yield of the sequence. n is an integer value comprised between 1 and 10 (limits included). In such an embodiment, the starting reaction mixture of the $(n+1)^{th}$ processing is the remaining mixture after the $n^{th}$ recovery of crystals, in particular the $n^{th}$ filtrate.

Step 3

Step 3 is the transformation of at least one isolated diastereoisomer of the tartrate salt into another salt.

Transformation of the tartrate salt into another salt, in particular a hydrochloride salt, is more specifically performed by reaction of the tartrate salt produced in step 1 and isolated in step 2 with the corresponding acid, in particular hydrochloric acid. The acid may be in solid, liquid and/or gaseous forms. In particular, the salt to be formed in step 3 is chosen so as to be insoluble in the reaction mixture and thus render easier the recovery of step 4.

The HX salt formed in step 3 is not necessarily the same salt as the HX salt that can be used as starting material of step 1.

Step 3 can be performed neat or in a solvent, it is preferably performed in a solvent.

The solvent of step 3 is more particularly chosen among water-miscible solvents such as alcohols, cetones, ethers such as tetrahydrofuran (THF) and methyltetrahydrofuran, water and mixtures thereof.

In an embodiment, the solvent is chosen among C1-C4 alcohols and mixtures thereof. Preferably, the solvent is chosen among methanol, ethanol, isopropanol and mixtures thereof. More preferably, the solvent is isopropanol or ethanol, in particular ethanol.

In another embodiment, the solvent is a ketone, preferably chosen among acetone, 2-butanone, 2-pentanone, 3-pentanone and mixtures thereof. In particular, the solvent is acetone.

Step 3 is preferably performed at atmospheric pressure and a temperature lower than 30° C., more preferably lower than 25° C., in particular to minimize the risk of formation of side-products.

The typical molar yield of step 3, performed once, is 50-55%.

Step 3 preferably leads to the crystallization of the desired salt of the triazine derivative. The experimental conditions of step 3 can be adjusted to monitor the crystallization. In particular, the experimental conditions can be adjusted to favour the crystallization of the salt. The other components of the reaction mixture remain for instance solubilised in the reaction medium.

Step 4

Step 4 is the recovery of the triazine salt obtained in step 3, preferably as crystals. Isolated crystals may be recovered more specifically by filtration, for instance using a dynamic filter dryer, or by centrifugation.

The process may further comprise at least one step of purification of the isolated diastereoisomeric tartrate salt of the triazine derivative. In particular, the purification step is between step 2 and step 3 of the process. This additional purification step can be more specifically performed by recrystallization in a suitable solvent or solvent mixture, or by washing with a suitable solvent. In a particular embodiment, this purification step aims at obtaining a desired specific diastereoisomeric purity.

The process may further comprise at least one step of purification of the isolated salt, in particular hydrochloride salt, of the triazine derivative. In particular, the purification step is after step 3 of the process. This additional purification step can be more specifically performed by recrystallization in a suitable solvent or solvent mixture, or by washing with a suitable solvent.

The process of the invention may be performed by batch or continuously. The process may involve recycling or re-processing of the excess reagents and subproducts of each step. For instance, the mother liquors of the filtration in step 2 may be further processed to increase the yield of step 2. Similarly, the mother liquors of step 3 may be processed to recover unreacted tartrate salt. Typically about 25-30% of the tartrate salt of the triazine derivative, in particular (+)-2-amino-3,6-dihydro-4-dimethylamino-6-methyl-1,3,5-triazine tartrate, may be recovered accordingly.

The percentage values in the present description correspond to molar percentages, unless specified otherwise.

Further aspects and advantages of the present invention will be disclosed in the following examples, which should be regarded as illustrative and not limiting the scope of this application.

DESCRIPTION OF THE FIGURES

FIG. 1: Global scheme of claimed process. FIG. 1 presents a specific embodiment of the process as specific enantiomers of tartaric acid and of the triazine derivative are represented.

EXAMPLES

Example 1

Synthesis and isolation of (+)-2-amino-3,6-dihydro-4-dimethylamino-6-methyl-1,3,5-triazine hydrochloride by the process according to the invention Preliminary step: Synthesis of racemic 2-amino-3,6-dihydro-4-dimethylamino-6-methyl-1,3,5-triazine hydrochloride

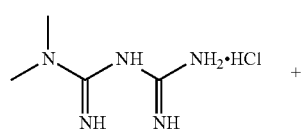

+

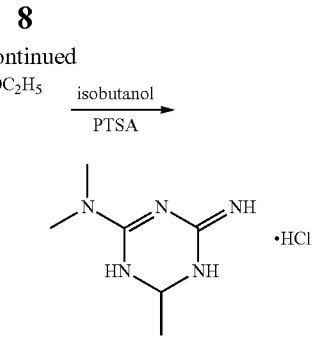

Metformin hydrochloride is suspended in 4 volumes of isobutanol. Acetaldehyde diethylacetal (1.2 eq.) and para-toluenesulfonic acid (PTSA) (0.05 eq) are added and the resulting suspension is heated to reflux until a clear solution is obtained. Then 2 volumes of the solvent are removed via distillation and the resulting suspension is cooled to 20° C. The formed crystals are isolated on a filter dryer and washed with isobutanol (0.55 volumes). Drying is not necessary and the wet product can be directly used for the next step.

Acetaldehyde diethylacetal can be replaced with 2,4,6-trimethyl-1,3,5-trioxane (paraldehyde).

Steps 1 and 2: Formation of the Diastereoisomeric Salt and Isolation of the Desired Diastereoisomer

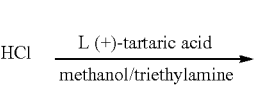

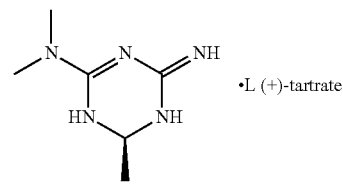

Racemic 2-amino-3,6-dihydro-4-dimethylamino-6-methyl-1,3,5-triazine hydrochloride wet with isobutanol (obtained as crude product from preliminary step without drying) and L-(+)-Tartaric acid (1 eq.) are dissolved in 2.2 volumes of methanol at 20-40° C. The obtained clear solution is filtered and then 1 equivalent of triethylamine (TEA) is added while keeping the temperature below 30° C. The suspension is heated to reflux, stirred at that temperature for 10 minutes and then cooled down to 55° C. The temperature is maintained at 55° C. for 2 hours and the suspension is then cooled to 5-10° C. After additional stirring for 2 hours at 5-10° C. the white crystals are isolated on a filter dryer, washed with methanol (2×0.5 Vol) and dried under vacuum at 50° C. The yield after drying is typically in the range of 40-45%

Steps 3 and 4: Transformation of the Isolated Diastereoisomer of the Tartrate Salt into the Hydrochloride Salt and Recovery of the Salt

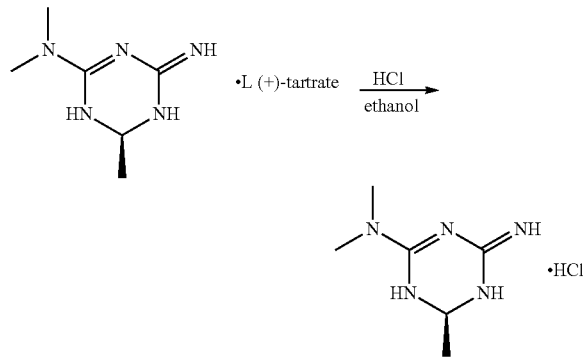

(+) 2-amino-3,6-dihydro-4-dimethylamino-6-methyl-1,3,5-triazine tartrate salt is suspended in 2 volumes of ethanol and 1.02 equivalents of HCl-gas are added under vacuum (≈500 mbar). The suspension is heated to reflux under atmospheric pressure ($N_2$) and 5% of the solvent is removed via distillation. Subsequent filtration of the clear colourless solution into a second reactor is followed by a cooling crystallization. the temperature is lowered to 2° C. The obtained suspension is stirred at 2° C. for 3 hours and afterwards the white crystals are isolated with a horizontal centrifuge. The crystal cake is washed with ethanol and dried under vacuum at 40° C. The typical yield is 50-55% and the mother liquors can be used for the recovery of about 25-30% of (+)-2-amino-3,6-dihydro-4-dimethyl amino-6-methyl-1,3,5-triazine tartrate.

Example 2

Modification of the Solvent of Steps 3 and 4

Steps 3 and 4: Transformation of the Isolated Diastereoisomer of the Tartrate Salt into the Hydrochloride Salt and Recovery of the Salt

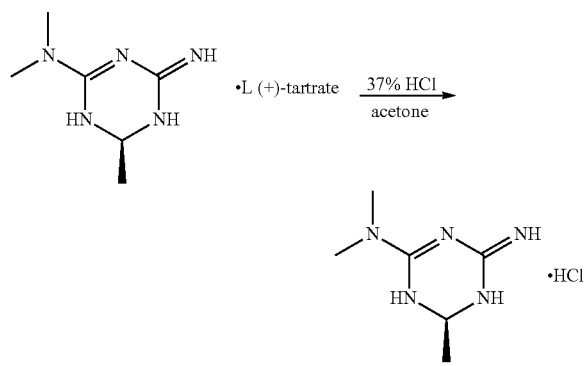

(+) 2-amino-3,6-dihydro-4-dimethylamino-6-methyl-1,3,5-triazine tartrate salt synthesized according to steps 1 and 2 of example 1 is suspended in 1 volume (based on total amount of (+) 2-amino-3,6-dihydro-4-dimethylamino-6-methyl-1,3,5-triazine tartrate salt) of acetone at 20° C. To this suspension 1.01 equivalents of 37% Hydrochloric acid are added. The suspension is heated to reflux under atmospheric pressure ($N_2$) and water is added until a clear solution is obtained. 1.5 vol of acetone are added at reflux temperature. The compound starts crystallising and the obtained suspension is kept at reflux for 2 hours followed by a cooling crystallization to 0° C. The obtained suspension is stirred at 0° C. for 2 hours and the white crystals are isolated by centrifugation. The crystal cake is washed with isopropanol and dried under vacuum at 40° C. in a continuous drying oven.

The invention claimed is:
1. A process for the separation of enantiomers of compounds of formula (I) below:

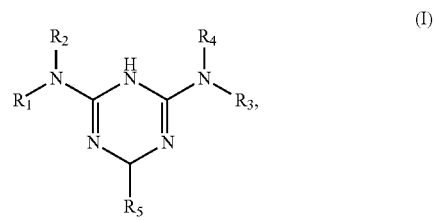

wherein:
$R_1, R_2, R_3$ and $R_4$ are chosen independently from the group consisting of the following groups:
  H;
  (C1-C20) alkyl optionally substituted by halogen, (C1-C5) alkyl, (C1-C5) alkoxy or (C3-C8) cycloalkyl;
  (C2-C20) alkylene optionally substituted by halogen, (C1-C5) alkyl or (C1-C5) alkoxy;
  (C2-C20) alkyne optionally substituted by halogen, (C1-C5) alkyl or (C1-C5) alkoxy;
  (C3-C8) cycloalkyl optionally substituted by (C1-C5) alkyl or (C1-C5) alkoxy;
  (C3-C8) heterocycloalkyl bearing one or more hetero atoms chosen from N, O and S and optionally substituted by (C1-C5) alkyl or (C1-C5) alkoxy;
  (C6-C14) arylalkyl (C1-C20) optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
  (C6-C14) aryl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl; or
  (C5-C13) heteroaryl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
$R_1$ and $R_2$, on the one hand, and $R_3$ and $R_4$, on the other hand, possibly forming with the nitrogen atom to which they are linked an n-membered ring (n between 3 and 8) optionally comprising one or more hetero atoms chosen from N, O and S and possibly being substituted by amino, hydroxyl, thio, halogen, (C1-C5) alkyl, (C1-C5) alkoxy, (C1-C5) alkylthio, (C1-C5) alkylamino, (C6-

C14) aryloxy, (C6-C14) arylalkoxy (C1-C5), cyano, trifluoromethyl, carboxyl, carboxymethyl or carboxyethyl;

$R_5$ is chosen from the group consisting of the following groups:
- (C1-C20) alkyl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C2-C20) alkylene optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C2-C20) alkyne optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C3-C8) cycloalkyl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C3-C8) heterocycloalkyl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C6-C14) aryl optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C5-C13) heteroaryl bearing one or more hetero atoms chosen from N, O and S and optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl;
- (C6-C14) arylalkyl(C1-C5) optionally substituted by amino, hydroxyl, thio, halogen, (C1-C5) alkyl, (C1-C5) alkoxy, (C1-C5) alkylthio, (C1-C5) alkylamino, (C6-C14) aryloxy, (C6-C14) arylalkoxy (C1-C5), cyano, trifluoromethyl, carboxyl, carboxymethyl or carboxyethyl, or a salt thereof, comprising the following steps:
- step 1: formation of a diastereoisomeric tartrate salt of the triazine derivative with a single enantiomer of tartaric acid by reaction of a salt of the compound of formula (I) with a single enantiomer of tartaric acid,
- step 2: separation of both diastereoisomers of the tartrate salt,
- step 3: transformation of at least one isolated diastereoisomer of the tartrate salt into another salt, and
- step 4: recovery of the triazine salt obtained in step 3.

2. The process according to claim 1, wherein at least one of $R_3$ and $R_4$ is a hydrogen atom.

3. The process according to claim 2, wherein $R_3$ and $R_4$ are both hydrogen atoms.

4. The process according to claim 1, wherein $R_1$ and $R_2$ independently represent C1 to C3 alkyl groups.

5. The process according to claim 4, wherein at least one alkyl group is methyl.

6. The process according to claim 1, wherein the compound of formula (I) is in the form of a salt.

7. The process according to claim 1, wherein the triazine derivative of formula (I) is chosen in the group consisting of:
- 2-amino-3,6-dihydro-4-dimethylamino-6-methyl-1,3,5-triazine,
- 2-amino-6-cyclohexyl-3,6-dihydro-4-dimethylamino-1,3,5-triazine, and a salt thereof.

8. The process according to claim 6, wherein the compound is 2-amino-3,6-dihydro-4-dimethylamino-6-methyl-1,3,5-triazine hydrochloride.

9. The process according to claim 1, wherein step 1 is performed with a salt of the triazine derivative as starting material.

10. The process according to claim 9, wherein a base is present in the reaction medium.

11. The process according to claim 10, wherein the base is triethylamine.

12. The process according to claim 1, wherein step 1 is performed by the reaction of a compound of formula (I) with L-(+)-tartaric acid.

13. The process according to claim 1, wherein step 1 is performed in a solvent.

14. The process according to claim 13, wherein the solvent of step 1 is methanol.

15. The process according to claim 1, wherein step 2 is performed by filtration or by centrifugation.

16. The process according to claim 1, wherein step 3 is performed in a solvent.

17. The process according to claim 16, wherein the solvent of step 3 is ethanol.

18. The process according to claim 1, wherein step 3 is performed in a solvent and the solvent of step 3 is acetone.

19. The process according to claim 6, wherein the salt is a hydrochloride salt.

* * * * *